United States Patent [19]
Matzinger et al.

[11] Patent Number: 5,968,836
[45] Date of Patent: *Oct. 19, 1999

[54] FLUID CONDUCTING TEST STRIP WITH TRANSPORT MEDIUM

[75] Inventors: David P. Matzinger, Menlo Park; Steven Zweig, Los Gatos; Yeung S. Yu, Pleasanton, all of Calif.

[73] Assignee: Lifescan, Inc., Milpitas, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/493,435

[22] Filed: Jun. 22, 1995

Related U.S. Application Data

[63] Continuation of application No. 08/230,447, Apr. 20, 1994, abandoned, which is a continuation of application No. 07/881,970, May 12, 1992, abandoned.

[51] Int. Cl.⁶ .................................................. G01N 21/77
[52] U.S. Cl. .............................. 436/169; 422/56; 422/58; 422/61; 436/178
[58] Field of Search ............... 422/56–61; 436/169–170, 436/177–178; 435/805; 210/506, 926

[56] References Cited

U.S. PATENT DOCUMENTS

| | | | |
|---|---|---|---|
| 3,607,093 | 9/1971 | Stone | 422/56 |
| 4,774,192 | 9/1988 | Terminiello et al. | 422/56 |
| 4,824,639 | 4/1989 | Hildenbrand et al. | 422/56 |
| 4,935,346 | 6/1990 | Phillips et al. | 435/14 |
| 4,987,085 | 1/1991 | Allen et al. | 422/58 |
| 4,994,238 | 2/1991 | Daffern et al. | 436/530 |
| 5,135,716 | 8/1992 | Thakare | 422/56 |
| 5,240,862 | 8/1993 | Koenhen et al. | 436/170 |

FOREIGN PATENT DOCUMENTS

| | | | |
|---|---|---|---|
| 297389 | 1/1989 | European Pat. Off. | G01N 33/52 |
| 297390 | 1/1989 | European Pat. Off. | G01N 33/52 |
| 0407800A3 | 1/1991 | European Pat. Off. | |

*Primary Examiner*—Lyle A. Alexander
*Attorney, Agent, or Firm*—James Riesenfeld

[57] ABSTRACT

A reagent strip is provided for measuring the concentration of an analyte in a liquid test sample, such as glucose or cholesterol in whole blood. The reagent strip includes a testing pad containing a color-forming reagent system specific to the analyte. The testing pad is disposed so that a side with relatively small pores defines a testing surface and an opposite side with relatively larger pores defines a sample-receiving surface. A porous sample transport medium is attached to the sample-receiving surface. A change in coloration caused by the color-forming reagent system at the testing surface is quantitatively related to the concentration of the analyte in the liquid test sample. The reagent strip may optionally include a rigid support member which facilitates evaluation of the change in coloration by mechanical viewing means. Also provided is a method for determining the concentration of an analyte in a liquid test sample.

26 Claims, 3 Drawing Sheets

FLUID CONDUCTING TEST STRIP WITH TRANSPORT MEDIUM

This is a continuation of application Ser. No. 08/230,447, filed Apr. 20, 1994, now abandoned, which is a continuation of application Ser. No. 07/881,970, filed May 12, 1992, now abandoned.

FIELD OF THE INVENTION

The present invention relates to a reagent strip which allows a user to quantitatively determine the concentration of an analyte in a liquid test sample. More specifically, the present invention relates to a reagent strip which combines a porous transport medium with a testing pad capable of quantitatively indicating the concentration of an analyte in a liquid test sample, such as glucose or cholesterol in whole blood.

BACKGROUND OF THE INVENTION

Numerous test devices have been developed for the analysis of body fluids in order to determine the concentration of specific analytes in test samples. These include devices for detecting, for example, glucose, cholesterol, proteins, ketones, uric acid, phenylalanine, or enzymes in either blood or urine. Often tests are used to diagnose or treat a particular disease, such as diabetes or high blood pressure.

Two general types of test strips are in common use. Older devices require the application of a drop of blood to the top surface of a reagent pad, allowing the drop to react for a timed interval, removing the drop by wiping or blotting, and then determining the analyte concentration either visually or through the use of a reflectance photometer. Newer devices simplify the procedure by allowing the user to apply a drop of blood to a test strip while it is inserted in a meter. Optical and electronic elements within the meter detect the presence of blood, automatically start a timing and measuring process, and complete the analysis without removal of blood from the strip.

While the commonly used test strips are widely acclaimed and entirely satisfactory for many applications, the user of such test strips must bring the finger from which the blood drop has been obtained to the meter, rather than simply bringing the strip to the finger. Also, the deep red coloration of blood in the strip can interfere with a visual confirmation of the amount of color formed. Visual confirmation is a desirable indication of proper operation of the meter which reinforces user confidence in the accuracy of the concentration measurement. These disadvantages can be especially troublesome when the user is a patient suffering from disabilities related to a disease, such as diabetes, who must determine his own analyte concentrations. Such patients may have difficulty performing mechanical procedures required to operate conventional reagent strips.

Accordingly, there exists a need for a reagent strip which provides a test that requires only a single step in which the user can apply an unmeasured sample of whole blood and determine the concentration level of an analyte in a whole blood sample, either visually or through electronic viewing means.

SUMMARY OF THE INVENTION

The invention provides a reagent strip for measuring the concentration of an analyte in a test sample. The reagent strip comprises a testing pad and a porous sample transport medium. The testing pad is formed from an anisotropic membrane which contains spatially separated regions having differently sized pores. One side of the testing pad has pores with relatively small effective diameters. The side with relatively small pores defines a testing surface. An opposite side with relatively larger pores defines a sample receiving surface. The testing pad contains a color-forming reagent system which reacts selectively with the analyte.

The transport medium is attached to the sample receiving surface of the testing pad. The transport medium is adapted to accept a whole blood sample and transport a detectable portion of the blood sample to the sample receiving surface. It is preferred that the transport medium be capable of holding from about 10 to about 50 microliters of blood, preferably about 35 microliters of blood and of passing from about 3 to about 10 microliters of blood to the testing pad.

The transport medium is connected to the testing pad by an adhesive layer, which may be a continuous layer formed along an outer edge of the testing pad, leaving a central portion of the testing pad substantially unobstructed. Alternatively, the adhesive layer may be discontinuous.

The reagent strip may optionally further comprise a rigid support member that defines an aperture which extends completely through the support member. The support member also defines a free surface adapted to contact and engage mechanical viewing means. The viewing means may be utilized in conjunction with or as an alternative to direct visual inspection for evaluating a change in coloration at the testing surface produced by the color-forming reagent system.

In another embodiment, adapted to facilitate evaluation primarily by mechanical viewing means after a color-change reaction, the reagent strip comprises a rigid support member, a testing pad, and a porous transport medium. The support member defines an aperture which extends through the support member. The support member has a free surface which is adapted to contact and engage viewing means. A portion of the support member disposed about the aperture has a predetermined and carefully controlled thickness which can be used to locate the testing surface at a reproducible distance from the viewing means.

The testing pad contains a color-forming reagent system which is specific to the analyte of interest. The testing pad is formed from an anisotropic membrane and has a side with relatively small pores that defines a testing surface. The testing pad also has an opposite side with relatively large pores which defines a sample-receiving surface. The testing surface is attached to the support member so that the testing surface faces and overlaps the aperture.

The transport medium is attached to the sample-receiving surface and is capable of accepting a whole blood sample. The transport medium transports a detectable portion of the sample to the sample-receiving surface where the color-forming reagent system causes a change in coloration which can be evaluated at the testing surface visually or by the use of viewing means, such as a reflectance meter. When the free surface of the support member is engaged by the viewing means, the testing surface is conveniently and reliably maintained at an optimum viewing distance relative to said viewing means. Concentration determinations performed while the free surface is engaged with the viewing means tend to be relatively more accurate and more reproducible.

It is preferred that the thickness of the portion disposed about the aperture be in the range of about 0.002 to about 0.040 of an inch. The testing pad preferably has pores which vary in size from about 25 micrometers on the side with relatively large pores to about 0.3 micrometer on the side with relatively small pores. The testing pad may be attached to the transport medium by a continuous adhesive positioned along an outer edge of the testing pad. Alternatively, the adhesive layer may be discontinuous and extend fully across the receiving surface.

The invention also provides a method for measuring the concentration of an analyte in a test sample. The method is especially suitable for test samples which contain solid color bodies. A test strip of the present invention is contacted with a transport medium. The transport medium absorbs the test sample, transports the test sample to the sample-receiving surface, and distributes the test sample across the sample-receiving surface.

At the receiving surface, the sample is absorbed into the testing pad. The sample moves through the testing pad, by capillary action, for example, and encounters progressively smaller pores as it approaches the testing surface. The smaller pores filter the test sample and remove at least some of the solid color bodies.

The testing reagent reacts chemically with the analyte to vary coloration of the testing surface. Coloration of the testing surface is compared to a calibrated color standard in order to determine the concentration of the analyte in the test sample.

The method may optionally further comprise the step of locating the testing surface a reproducible distance from a mechanical viewing means by contacting the viewing means with a free surface of a rigid support member attached to the testing surface.

These and other features of the invention will be better understood in connection with the following drawings and detailed description of the preferred embodiments.

DETAILED DESCRIPTION OF THE PREFERRED EMBODIMENTS

Figure 1:
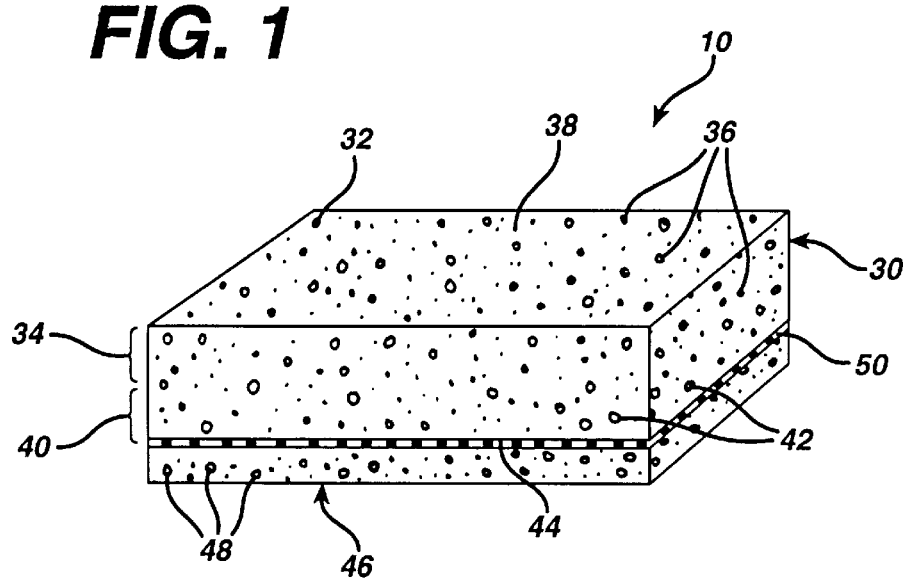
FIG. 1 is a perspective view of a preferred embodiment of a reagent strip of the present invention.

Whole blood samples can be applied to one side of the reagent strip of the present invention and a visual comparison of the analyte concentration level can be made at the opposite side of the reagent strip. Preferably, the color developed in the reagent strip is stable for an extended period of time. In order to facilitate either visual or electronic interpretation, the reagent strip absorbs excess blood beyond that needed for the test, thus preventing contamination of the viewing means and adjacent areas. When determination of the concentration is to be done through electronic viewing means, the reagent strip is adapted to be conveniently brought to the surface of a whole blood sample and, thereafter, positively and reproducibly engaged with the viewing means, without the complications of timing or blood removal.

A reagent strip in accordance with the present invention comprises a testing pad and a transport medium. The testing pad is formed from an anisotropic membrane which has a small pore side and a large pore side. For present purposes, an anisotropic membrane is a membrane which has one or more differentiable spatial regions, characterized by a different nominal effective pore diameter. In the testing pad of the present invention, the anisotropic membrane is oriented so that a side which defines a sample receiving surface has relatively larger pores than an opposite side which defines a testing surface.

The thickness of the testing pad will be sufficient to permit the formation of a colored reaction product on a testing surface of the testing pad which is opposite a side with relatively larger pores which defines a sample receiving surface. A membrane having a thickness in the range of about 50 to about 500 microns is usually employed as the testing pad, with a thickness in the range of about 100 microns to about 200 microns being preferred. The testing pad has pores with effective diameters in the range of about 0.1 to 1.0 micron, preferably about 0.3 to 0.6 micron, on the small pore side. The large pore side has spores with effective diameters in the range of about 5 to about 50 microns, with about 10 to about 20 microns being preferred.

When blood separation is effected, most of the colored components of whole blood reach a point in the anisotropic membrane where relatively smaller pores prevent the colored components from penetrating further into the membrane. The balance of the sample is a relatively clear fluid containing an analyte of interest which can penetrate completely through the membrane. A color change relating to the concentration of an analyte in whole blood can be read, visually or by viewing means, on the underside of the membrane substantially free from interference caused by the highly colored blood components which are separated in the anisotropic membrane.

The testing pad does not deform substantially upon wetting and, preferably, is relatively incompressible. The testing pad may be composed of porous polyamides, polysulfones, polyesters, polyolefins, or cellulosics. Polysulfone is the preferred material for the testing pad.

The transport medium is a porous medium adapted to accept a whole blood sample and transport a detectable portion of the sample to the sample receiving surface. The sample is absorbed into the pores of the transport medium and passed through the medium by, for example, capillary action. The transport medium may be composed of natural fibers, such as cotton or paper, as well as polyesters, polyamides, polyethylene, and other synthetic polymers. Polyethylene is the preferred transport medium material.

The transport medium has pores having an effective diameter in the range of about 20 microns to about 200 microns, preferably about 50 to about 100 microns. The transport medium is generally hydrophilic or may be rendered hydrophilic by treatment with surfactants compatible with red blood cells. One such compatible surfactant is MAPHOS™ 66 sold by Mazer Chemical, a division of PPG Industries Inc. Chemicals of Gurnee, Ill. In a preferred embodiment, the transport medium is capable of absorbing blood samples of up to about 35 to about 40 microliters.

The transport medium may be, for example, a filter paper or sintered plastic material, such as those porous polyethylene materials commonly available from the Porex Corp. of Fairburn, Ga. The transport medium is generally fabricated to have a thickness of about 0.025 inch, with about 0.25 inch width and about 1.0 inch length. The transport medium is treated with a red blood cell compatible surfactant solution. Since only about 3 to about 5 microliters of blood are required to saturate the testing pad, the transport medium will preferably possess a small void volume in order not to require large volumes of blood. Excess blood applied to the reagent strip is absorbed and held in a portion of the transport medium which may extend beyond the testing pad.

The testing pad is attached to the transport medium by an adhesive layer. Emulsion-based pressure-sensitive adhesives are preferred for this service, including acrylic, rubber, and ethylene vinyl acetate (EVA) based formulations. A suitable rubber adhesive is sold under the trade designation Unitak 13125 and a suitable EVA adhesive is sold under the trade designation Vetak G80525, both of such products being commercially available from Imperial Adhesives of Cincinnatti, Ohio. An acrylic adhesive commercially available from Century Adhesives of Columbus, Ohio under the tradename C-800 is especially preferred. However, all of the adhesives tested were excessively hydrophobic and tended to impede the passage of blood through the adhesive layer. Mixing about 10 g of C-800 adhesive with about 0.1 g of fumed silica and 0.15 milliliter of a solution containing sodium dodecyl sulfate, isopropanol, and water produced an adhesive with optimum characteristics.

The adhesive may be placed in continuous strips located only near the perimeter of the test pad, leaving a central portion of the receiving surface of the test pad substantially unobstructed. Alternatively, the adhesive layer may be in the form of a discontinuous array of adhesive in the form of dots, patterns, or thin lines. If dots of adhesive are used, it is preferred that they be arranged so that there are about 60 to 70 dots to the inch. The dots may be placed by use of a silk screening process. The discontinuous adhesive layer may also be fabricated from commercially available adhesive products deposited from a release lining.

It is preferred that the adhesive be applied in a discontinuous adhesive layer by a printing process such as flexography. A continuous thin film of adhesive is applied to the porous transport medium so that the adhesive coats only the points of the surface which contact a printing roller or printing plate surface. Adhesive does not bridge the pores. Consequently, the discontinuous pattern of adhesive precisely complements the pattern of pores on the surface of the porous transport medium. Suitable adhesives for this process may include pressure-sensitive, wet-bond, or hot-melt adhesives. The printing process is described in more detail below.

Alternatively, when the transport layer is composed of a material that fuses at industrially practical temperatures, the transport layer may be attached directly to the testing pad by an application of heat and pressure. The transport layer is heated until it begins to melt and then pressed against the testing pad and cooled. Direct attachment of the transport layer to the testing pad by fusion obviates any need for a distinct adhesive layer.

The porous adhesive layer connects the transport medium to the sample receiving surface of the testing pad. The transport medium is adapted to accept a whole blood sample and transport a detectable portion of the sample to the receiving surface. The sample may be moved by capillary action. The transport medium preferably extends past one or more ends of the testing pad so as to form a reservoir for holding excess amounts of blood sample which may be present during actual use. It is usually more desirable to retain such excess amounts of the blood sample in the transport medium, rather than allowing the excess to drip upon the user or upon the viewing means in an uncontrolled fashion. Accordingly, it is preferred that the transport medium be capable of holding from about 10 to about 50 microliters of blood, preferably about 35 microliters of blood and of passing from about 3 to about 10 microliters of blood to the testing pad.

The testing pad is impregnated with a color forming reagent system specific to an analyte. Typical analytes are glucose, cholesterol, urea, and many others which will readily occur to those ordinarily skilled in the art. Preferably, the color forming reagent system includes an enzyme which selectively catalyzes a primary reaction with the analyte of interest. A product of the primary reaction may be a final dye which undergoes a change in color that is detectable at the testing surface. Alternatively, the product of the primary reaction may be an intermediate which undergoes another reaction, preferably also enzyme catalyzed, and participates in a secondary reaction which, directly or indirectly, causes a final dye to undergo a change in color which is detectable at the testing surface.

An exemplary color-forming reagent system is the system which is specific to glucose and contains glucose oxidase, a peroxidase, and an oxidizable dye. Glucose oxidase is an enzyme, usually obtained from *Aspergillus niger* or Penicillium, that reacts with glucose and oxygen to produce gluconolactone and hydrogen peroxide. The hydrogen peroxide so produced is catalyzed by a peroxidase enzyme, such as horseradish peroxidase, in the presence of final dye, such as alizarin cyanin green or anazolene sodium. The final dye exhibits a color change that may be observed at the testing surface. Many other suitable color-forming reagent systems specific to particular analytes are known in the art.

The testing pad is adapted to receive a whole blood sample at the sample receiving surface and transport a liquid portion of the whole blood sample toward the testing surface. The liquid portion of the sample is moved by capillary action. However, red blood cells included in the whole blood sample are substantially separated from the liquid portion of the sample as it moves through the testing pad.

As the whole blood sample penetrates the testing pad, it encounters progressively smaller pores which serve to filter red blood cells and other color forming particles from the sample. The liquid portion of the sample which reaches the testing surface is substantially clear and does not interfere with the user's evaluation of any change in coloration caused by the color-forming reagent system at the testing surface.

The color-forming reagent system is adapted to produce a quantitative change in coloration at the testing surface which is a function of the concentration of the analyte in the whole blood sample. Although it is preferred that the change in coloration is detectable by the naked eye, the color change may be evaluated visually or through the use of viewing means, or both. A reflectance meter is a typical form of viewing means.

Referring now to FIG. 1, a preferred reagent strip 10 includes a testing pad 30 which is formed from an anisotropic membrane 32. The testing pad 30 has a side 34 which contains relatively small pores 36. The side 34 with relatively small pores defines a testing surface 38.

The testing pad 30 also has an opposite side 40 having relatively large pores 42. The side 40 with relatively large pores defines a sample receiving surface 44.

A transport medium 46 is attached to the sample receiving surface 44. The transport medium 46 contains relatively large pores 48. Connecting the transport medium 46 to the sample receiving surface 44 is an adhesive layer 50. Preferably, the adhesive layer 50 is discontinuous.

In another embodiment of the invention, the reagent strip includes a rigid support member which is attached to a testing pad. The support member may be fabricated of nylon-coated paper, MYLAR™, and other materials which are chemically inert and relatively rigid.

The rigid support member defines an aperture which passes completely through the rigid support member. A portion disposed about the aperture has a carefully controlled and predetermined thickness which is in the range of about 0.002 to about 0.050 of an inch thick, preferably about 0.010 to about 0.020. At least one surface defined by the support member is a surface adapted to positively and reproducibly contact an engaged viewing means.

A significantly higher degree of reproducibility can be obtained when the reagent strip of the present invention is evaluated using viewing means, such as a reflectance meter, located a precisely controlled distance from a testing surface of a testing pad. Objective viewing means are generally more reproducible than visual examination by subjective human eyes. In addition, it has been found that small differences in the distance between the testing surface and a lens of the viewing means can cause significant changes in determination results.

Accordingly, the rigid support member is fabricated with a portion disposed about the aperture having a carefully controlled thickness. When the surface of the support member is engaged with the viewing means, the distance between the viewing means and the testing pad is conveniently and reliably set. Of course, other advantages accrue from the incorporation of the support member. For example, the support member can act as a shield which protects the viewing means from contact with the liquid sample carried by the testing pad.

The testing pad and an adhesive layer which attaches the sample-receiving surface of the testing pad to a transport medium are as described above.

The transport medium is substantially as described above. However, the transport medium may extend beyond the edges of the testing pad to form regions which do not contact the testing pad and are useful for storing excess sample. The regions which extend beyond the testing pad are preferably attached to the support member.

Figure 2:
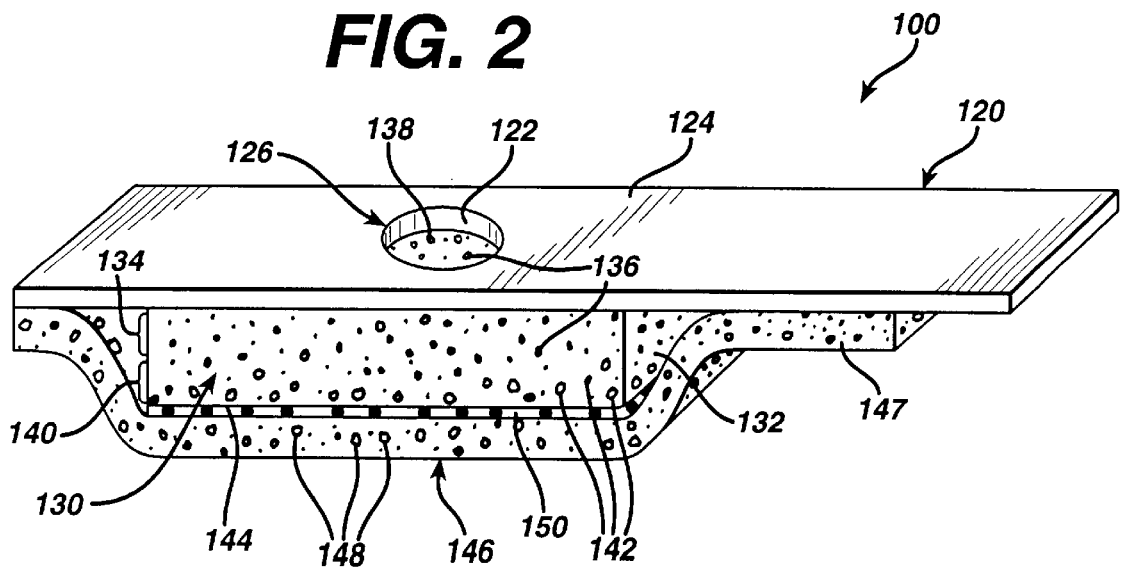
FIG. 2 is a perspective view of another preferred embodiment of a reagent strip of the present invention.

FIG. 2 illustrates a preferred reagent strip 100 having a rigid support member 120 defining an aperture 122 and a free surface 124. The free surface 124 is adapted to engage viewing means (not shown). A portion 126 of the support member which surrounds the aperture 122 is fabricated with a known and carefully controlled thickness.

A testing pad 130 is attached to the support member 120 so that the testing pad 130 overlaps the aperture 122. The testing pad 130 is formed from an anisotropic membrane 132 having a side 134 with relatively small pores 136 and a side 140 with relatively large pores 142. At least a portion of the testing surface 138 abuts the aperture 122. The side 134 with relatively small pores defines a testing surface 138 which faces the support member 120. The side 142 with relatively larger pores defines a sample-receiving surface 144.

An adhesive layer 150, which is preferably discontinuous, connects the sample receiving surface 144 to a transport medium 146. The transport medium 146 extends beyond the testing pad 130, having a region 147 which does not contact the testing pad 130. The region 147 is useful as a storage reservoir for excess amounts of a blood sample. The transport medium 146 contains a multitude of relatively large pores 148.

Figure 3:
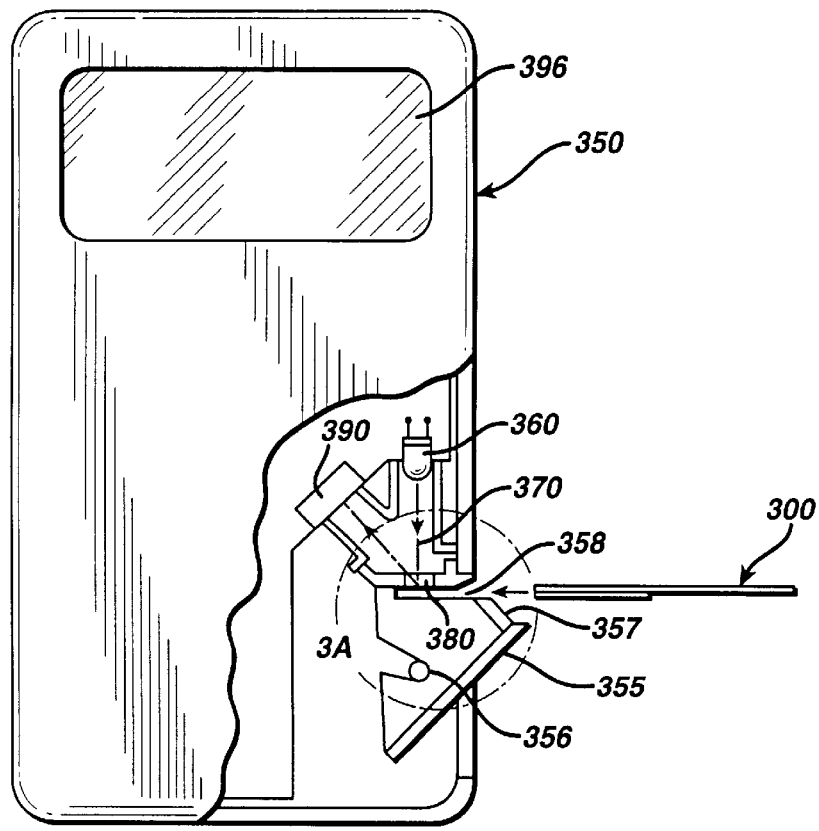
FIG. 3 is a partially cutaway elevation view of a viewing means with a reagent strip positioned to enter and engage the viewing means.

While the viewing means is not a part of the present invention, an example of a suitable viewing means is illustrated in FIG. 3 in which a reagent strip 300 of the present invention is inserted into a viewing means 350. The viewing means 350 is a hand-held reflectance meter, battery operated and equipped with display means 396. FIG. 3 depicts the orientation of the reagent strip 300 with the viewing means 350 just before insertion. An arrow in FIG. 3 indicates a direction of movement to bring the reagent strip into engagement with the viewing means 350.

A rotatable member 355 turns on an axis about a pin 356 to present a calibration surface 357 to a light source 360. Alternatively, the rotatable member 355 may be rotated to open a port 358 in which the reagent strip 300 may be inserted. The calibration surface 357 may be, for example, an unblemished white surface, having a reflectance of approximately 100 percent. Alternatively, the calibration surface 357 may be a flat black surface representing zero percent reflectance for calibration purposes.

Figure 3A:
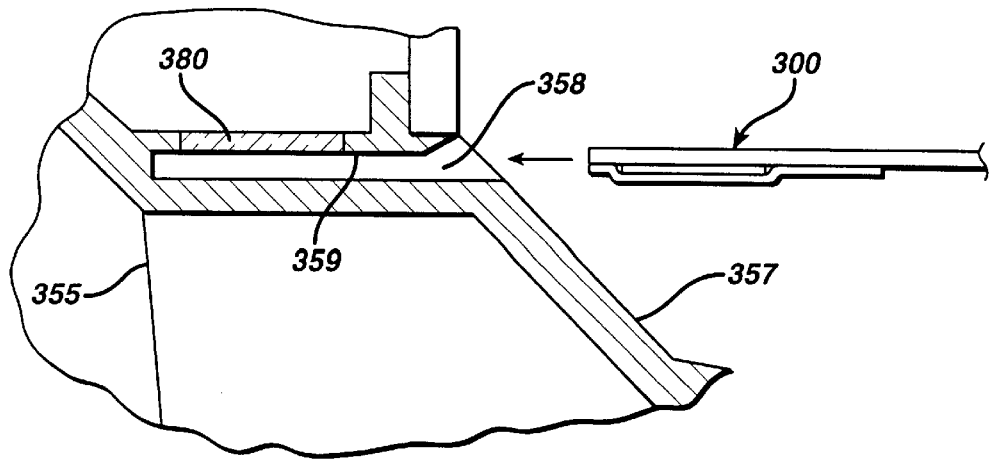
FIG. 3A is an enlarged partial cross-sectional view of the viewing means and the reagent strip of FIG. 3.

When the reagent strip 300 is inserted into the port 358, a free surface of the support member contacts and engages a mating surface 359 which is illustrated in FIG. 3A. When the reagent strip is engaged, light rays 370 from the light source 360 pass through a window striking the testing surface of the reagent and reflecting to a light sensor 390. A signal from the light sensor will be electronically compared to similar signals received by the light sensor 390 when the calibration surface 357 is presented to the light source 360. The difference in signals is quantitatively related to the concentration of an analyte in a blood sample on the reagent strip 300, according to a predetermined mathematical formula. The concentration so determined is indicated digitally on the display means 396.

When the reagent strip is intended to be inserted into a meter, blood must be absorbed by the reagent strip and retained so that it does not soil the meter with repeated use. The major reservoir for blood in the reagent strip is the transport medium. After complete absorption of the sample, blood is held in the transport medium as in a sponge. Unlike a sponge, however, the presently favored material, surfactant-treated porous polyethylene of the type commercially obtainable from Porex Corporation, is essentially incompressible, and blood is not squeezed out. However, since the surfactant treatment renders the polyethylene completely wettable, a film of blood remains in the outer surface of the material. When an object comes in contact with this film, surface tension can draw blood back out of the transport medium, contaminating the object.

It has been found that printing a film of hydrophobic polymer onto the sample accepting surface of the transport medium, preferably by flexographic printing, improves the blood retention properties of the reagent strip. When an appropriate polymer is applied, blood is absorbed into the transport medium, but does not transfer back to external contacting surfaces, even when moderate pressure and sliding actions are applied. A preferred hydrophobic polymer for this treatment is GAF ES-225, obtainable from GAF Chemicals Corp. of Irvine, Calif., which is a monomethyl ether of poly(methylvinyl ether/maleic acid). For example, a 30 W % ES-225 solution in ethanol can be printed onto the transport medium using the flexographic printing method.

Another way to improve the blood retention of the reagent strip is to modify the surface of the transport medium by chemical reaction in such a way that its surface energy is higher (more water-wettable) than that of the native polyethylene, but not as high as the surfactant-treated material. Blood is then drawn into the transport medium, but will not be drawn out by contacting surfaces.

The surface energy of a polyethylene transport media can be suitably modified by corona-discharge, which modifies polymer surfaces by introducing polar, oxygen-containing groups into the polymer chains at the surface. Alternatively, other means of suitably chemically modifying the polymer surface may be employed, such as other plasma treatments or solution-based treatments. Polymers other than polyethylene can be employed to form the transport medium, with a native surface energy such that no treatment is necessary.

The invention also provides a method for measuring the concentration of an analyte in a test sample. The method is especially suitable for use with test samples that contain solid color bodies, such as red blood cells. A reagent strip is provided which includes a testing pad in which pores are anisotropically arranged to produce a gradient in effective pore size which extends from a sample-receiving surface to a testing surface of the testing pad. Pores closer to the testing surface are generally smaller than those further from the testing surface. A porous sample transport medium is attached to the sample receiving surface.

A test sample, preferably of a biological fluid having solid color bodies, which contains the analyte is contacted with the transport medium. The transport medium absorbs the test sample, transports the test sample to the receiving surface, and distributes the test sample transversely relative to a direction in which the test sample is moved.

The test sample enters the testing pad at the sample-receiving surface. Once inside the testing pad, the test sample is further transported toward the testing surface. As it travels along the gradient of pore sizes, the test sample encounters progressively smaller pores. The smaller pores filter the test sample and at least some solid color bodies are separated from the test sample. The portion of the test sample which reaches the testing surface contains relatively few solid color bodies.

The testing reagent chemically reacts with the analyte to produce a change in coloration which is detectable at the test surface. The change in coloration is evaluated by comparing the coloration of the test surface to a calibrated color standard. The color standards are prepared in advance using data from testing pads and transport mediums exposed to samples having known concentrations.

The method may optionally further comprise the step of locating the testing surface a reproducible distance from a mechanical viewing means by contacting the viewing means with a free surface of a rigid support member attached to the testing surface. The rigid support member has been described above. The testing pad is attached to the support member so that at least a portion of the testing surface overlaps the aperture and is exposed to the viewing means.

Figure 4:
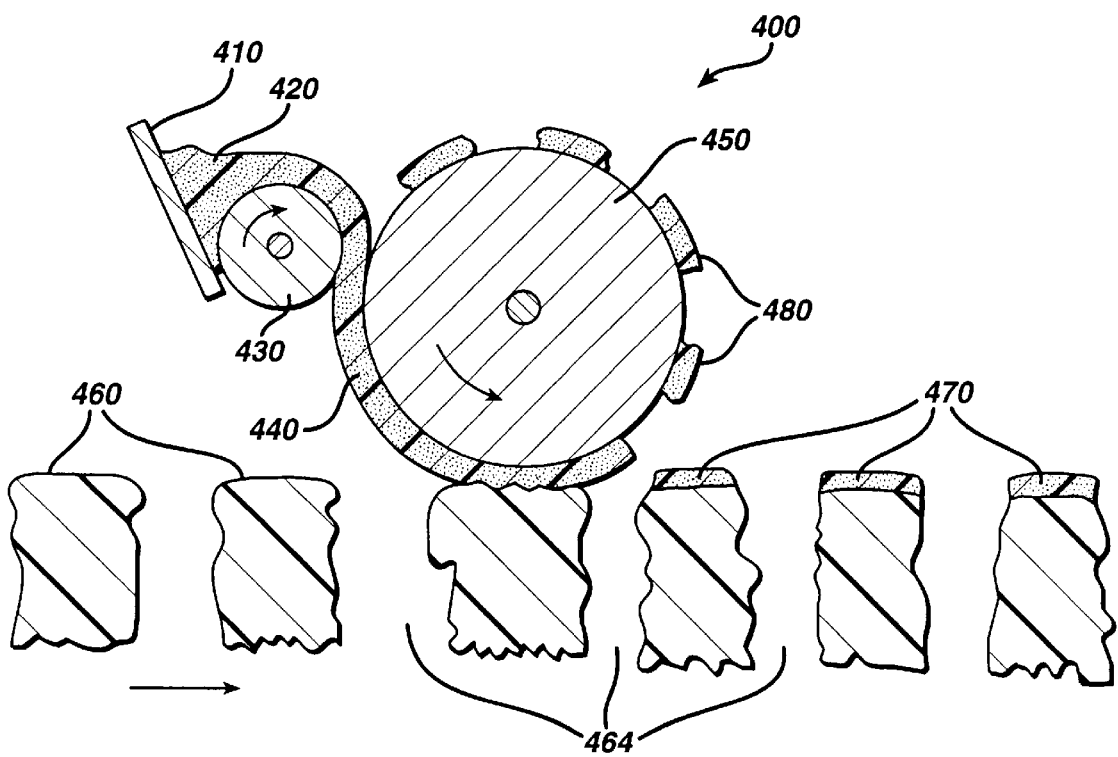
FIG. 4 is a cross-sectional view, not to scale, illustrating a printing process for applying a discontinuous adhesive layer to a receiving surface of a porous testing pad, suitable for use in fabricating a reagent strip of the present invention.

FIG. 4 is a cross-sectional view of a printing system 400 for applying a discontinuous adhesive layer to a surface of a porous transport medium. Although not essential to the invention, a flexographic printing system, such as the printing system 400, is a convenient means of applying a discontinuous adhesive layer which does not bridge pores of the transport medium.

Referring now to FIG. 4, a doctor blade 410 forms a reservoir in which an adhesive supply 420 is temporarily held. An anilox roller 430 turning counterclockwise as seen in FIG. 4, transfers a continuous film 440 of adhesive to a printing roller 450. The anilox roller 430 is a steel cylinder with tiny engraved, closely spaced pits which transfer a predetermined amount of adhesive liquid from the adhesive supply 420 to the printing roller 450. The printing roller 450 turns clockwise as seen in FIG. 4.

A surface 460 of the transport medium is brought into contact with the continuous thin film 440, moving relative to the printing roller 450 from left to right as depicted in FIG. 4. The surface 460 is made to approach the printing roller 450 at a distance and with a speed which causes the continuous thin film 440 to adhere to the surface 460 but not bridge pores 464. Accordingly, a discontinuous adhesive layer 470 which does not bridge the pores 464 is applied to the surface 460.

A continuous thin film 440 does not completely leave the printing roller 450. Some remaining adhesive 480 does not adhere to the receiving surface 460 but is instead carried along by the rotation of the printing roller 450, and eventually returned to the continuous thin film 440.

Descriptions of the invention and examples of its use have been set forth to communicate the invention fully, not to limit the scope of the invention in any way. As should be apparent to those of ordinary skill who study the specification, the invention may be practiced in various embodiments. The scope of the invention is intended to be as broad as the claims will allow.

What is claimed is:

1. A reagent strip for measuring the concentration of an analyte in a test sample, suitable for evaluation by the human eye or by mechanical viewing means, consisting essentially of:

a testing pad formed from an anisotropic membrane impregnated with a color-forming reagent system specific to an analyte and having a side with relatively small pores which defines a testing surface and an opposite side with relatively large pores which defines a sample receiving surface; and a porous sample transport medium attached to the sample receiving surface of the testing pad, said transport medium being capable of accepting a whole blood sample on a sample accepting surface and transporting a detectable portion of the sample to the sample receiving surface.

2. The reagent strip of claim 1 wherein the sample accepting surface of the transport medium is coated with a film containing a hydrophobic polymer.

3. The reagent strip of claim 1 wherein the transport medium is capable of holding about 35 microliters of blood and of passing about 3 microliters of blood to said testing pad.

4. The reagent strip of claim 1 wherein the transport medium has pores which are in the size range of about 20 to about 200 micrometers.

5. The reagent strip of claim 1 wherein the transport medium is composed of polyethylene.

6. The reagent strip of claim 1 wherein the testing pad has pores in the size range of about 5 to about 50 micrometers on the side with relatively large pores decreasing to about 0.1 to about 1.0 micrometer on the side with relatively small pores.

7. The reagent strip of claim 1 wherein the testing pad is composed of polysulfone.

8. The reagent strip of claim 1 wherein an adhesive layer formed along an outer edge of the testing pad is attached to the testing pad and the transport medium.

9. The reagent strip of claim 1 wherein a discontinuous adhesive layer is positioned between and attached to the testing pad and the transport medium.

10. The reagent strip of claim 1 which further comprises a rigid support member defining an aperture therethrough and having a free surface adapted to contact and engage mechanical viewing means.

11. The reagent strip of claim 10 wherein the transport medium includes a region that does not contact the testing pad.

12. A reagent strip for measuring the concentration of an analyte in a test sample suitable for evaluation primarily by mechanical viewing means, consisting essentially of:

a rigid support member defining an aperture therethrough and having a surface adapted to contact and engage viewing means and a portion disposed about the aperture with a predetermined thickness;

a testing pad formed from an anisotropic membrane impregnated with a color-forming reagent system specific to an analyte and having a side with relatively small pores which defines a testing surface and an opposite side with relatively large pores which defines a sample receiving surface, said testing surface being attached to said support member so that the testing surface faces and overlaps the aperture; and a porous sample transport medium attached to the sample receiving surface of the testing pad, said transport medium being capable of accepting a whole blood sample and transporting a detectable portion of the sample to the sample receiving surface;

whereby the testing surface is maintained at an optimum viewing distance relative to said viewing means when the free surface of the support member engages said viewing means.

13. The reagent strip of claim 12 wherein the portion of the support member disposed about the aperture has a thickness in the range of about 0.002 to about 0.050 of an inch.

14. The reagent strip of claim 12 wherein the transport medium is capable of holding about 35 microliters of blood and of passing about 3 microliters of blood to said testing pad.

15. The reagent strip of claim 12 wherein the transport medium has pores which are in the size range of about 20 to about 200 micrometers.

16. The reagent strip of claim 12 wherein the transport medium is composed of polyethylene.

17. The reagent strip of claim 12 wherein the testing pad has pores in the size range of about 5 to about 50 micrometers on the side with relatively large pores decreasing to about 0.1 to about 1.0 micrometer on the side with relatively small pores.

18. The reagent strip of claim 12 wherein the testing pad is composed of polysulfone.

19. The reagent strip of claim 12 wherein an adhesive layer formed along an outer edge of the testing pad is attached to the testing pad and the transport medium.

20. The reagent strip of claim 12 wherein a discontinuous adhesive layer is positioned between and attached to the testing pad and the transport medium.

21. A method for measuring the concentration of an analyte in a test sample containing solid color bodies which comprises:

providing a reagent strip which consists essentially of a testing pad formed from a porous anisotropic membrane impregnated with a color-forming reagent system specific to an analyte which defines a testing surface and a sample receiving surface, and a porous sample transport medium attached to the sample-receiving surface;

contacting a test sample of a biological fluid which contains the analyte and solid color bodies with the transport medium;

absorbing the test sample into the transport medium, transporting the test sample to the sample receiving surface, and distributing the test sample across the sample-receiving surface;

transporting and filtering the test sample through the testing pad in a direction which exposes the sample to progressively smaller pores, separating at least some of the solid color bodies from the test sample; and chemically reacting the testing reagent with the analyte to vary coloration of the testing surface INS H1.

22. The method of claim 21 in which the coloration of the testing surface is compared to a calibrated color standard to determine the concentration of the analyte in the test sample.

23. The method of claim 21 which further comprises locating the testing surface a reproducible distance from a viewing means by contacting the viewing means with a rigid support member which has a controlled thickness, defines an aperture, and abuts the testing surface.

24. A reagent strip for measuring the concentration of an analyte in a liquid sample which exhibits an optically visible color change as a function of the concentration of said analyte in said sample, consisting essentially of:

a relatively rigid support member having opposed first and second major surfaces and having an aperture therethrough;

a testing pad overlying said aperture on said first major surface, said testing pad having a sample receiving surface and an opposed testing surface, with said testing surface in face-to-face relationship with said first major surface of said support and with a portion of said testing surface being optically visible through said aperture;

said testing pad formed from a porous anisotropic membrane, said pores decreasing in effective diameter from said sample receiving surface to said testing surface;

said testing pad impregnated with reactants selected to react with said analyte if present in said testing pad to produce a color change visible at said testing surface;

a porous sample transport medium overlying said sample receiving surface of said testing pad and having portions extending beyond the perimeter of said testing pad to overlie, in face-to-face contact, the first surface of said support member;

whereby said liquid sample may be applied to said transport medium, a portion of said sample may be transported to the sample receiving surface of said testing pad and a portion of said sample may be transported through said testing pad, wherein analyte if present will react with said reactants in said testing pad and any resulting color change will be visible on the testing surface through said aperture, and whereby said portion of the transport medium extending beyond the perimeter of the testing pad provides a reservoir for excess liquid sample applied to the transport surface.

25. The test pad of claim 24 wherein the transport medium comprises essentially incompressible material to ameliorate the unintended expulsion of applied liquid sample.

26. The test pad of claim 25 wherein the outer surface of said transport medium is hydrophobic with respect to the remainder of the transport medium.

* * * * *